United States Patent
Hong et al.

(10) Patent No.: US 11,779,257 B2
(45) Date of Patent: Oct. 10, 2023

(54) 3-DIMENSIONAL MEASUREMENT METHOD FOR EYE MOVEMENT AND FULLY AUTOMATED DEEP-LEARNING BASED SYSTEM FOR VERTIGO DIAGNOSIS

(71) Applicant: Hallym University Technology Holdings, Anyang-si (KR)

(72) Inventors: Sung Kwang Hong, Seongnam-si (KR); Eun Cheon Lim, Anyang-Si (KR); Jeong Hye Park, Seoul (KR)

(73) Assignee: HALLYM UNIVERSITY TECHNOLOGY HOLDINGS, Anyang-si (KR)

( * ) Notice: Subject to any disclaimer, the term of this patent is extended or adjusted under 35 U.S.C. 154(b) by 1152 days.

(21) Appl. No.: 16/465,608

(22) PCT Filed: Apr. 26, 2018

(86) PCT No.: PCT/KR2018/004844
§ 371 (c)(1),
(2) Date: May 31, 2019

(87) PCT Pub. No.: WO2019/208848
PCT Pub. Date: Oct. 31, 2019

(65) Prior Publication Data
US 2020/0345288 A1 Nov. 5, 2020

(30) Foreign Application Priority Data
Apr. 24, 2018 (KR) .......................... 10-2018-0047505

(51) Int. Cl.
*A61B 5/00* (2006.01)
*A61B 3/00* (2006.01)
(Continued)

(52) U.S. Cl.
CPC .......... *A61B 5/4023* (2013.01); *A61B 3/0025* (2013.01); *A61B 3/0091* (2013.01);
(Continued)

(58) Field of Classification Search
CPC ... A61B 5/4023; A61B 3/0025; A61B 3/0091; A61B 3/113; A61B 3/145; A61B 5/7267; A61B 5/7282
(Continued)

(56) References Cited

U.S. PATENT DOCUMENTS 7,401,920 B1 * 7/2008 Kranz ................ G02B 27/0093
382/117
7,465,050 B2 12/2008 Migliaccio et al.
(Continued)

FOREIGN PATENT DOCUMENTS

KR 20010018719 A 3/2001
KR 20040107677 A 12/2004
(Continued)

OTHER PUBLICATIONS

International Search Report issued in corresponding International Application No. PCT/KR2018/004844 dated Oct. 26, 2018 (4 pages).

*Primary Examiner* — James R Greece
(74) *Attorney, Agent, or Firm* — Goldilocks zone IP Law

(57) ABSTRACT

The present invention relates to an eye movement measurement method including the steps of: (a) presenting standardized nystagmus test items and receiving am image of an eye in accordance with the standardized nystagmus test items; (b) recognizing a pupil and an iris from the image of the eye; (c) calculating amounts of horizontal and vertical changes of the pupil and an amount of torsional movement of the iris; (d) determining change values and orientations for three axis directions of the eye on the basis of the amounts of the
(Continued)

horizontal and vertical changes of the pupil and the amount of the torsional movement of the iris; and (e) generating a diagnosis result for vertigo through deep learning modeling on the basis of the change values and orientations of the three axis directions of the eye.

15 Claims, 8 Drawing Sheets

(51) Int. Cl.
    *A61B 3/113*     (2006.01)
    *A61B 3/14*     (2006.01)

(52) U.S. Cl.
    CPC .............. *A61B 3/113* (2013.01); *A61B 3/145* (2013.01); *A61B 5/7267* (2013.01); *A61B 5/7282* (2013.01)

(58) Field of Classification Search
    USPC ........................................................ 600/408
    See application file for complete search history.

(56) References Cited

U.S. PATENT DOCUMENTS

| | | |
|---|---|---|
| 2014/0243651 A1 | 8/2014 | Kim et al. |
| 2018/0174309 A1 | 6/2018 | Hoshino |

FOREIGN PATENT DOCUMENTS

| | | | |
|---|---|---|---|
| KR | 101297330 B1 | | 8/2013 |
| KR | 20140108417 A | | 9/2014 |
| KR | 20140141917 A | * | 12/2014 |
| WO | 2016195066 A1 | | 12/2016 |

* cited by examiner

[FIG. 1]
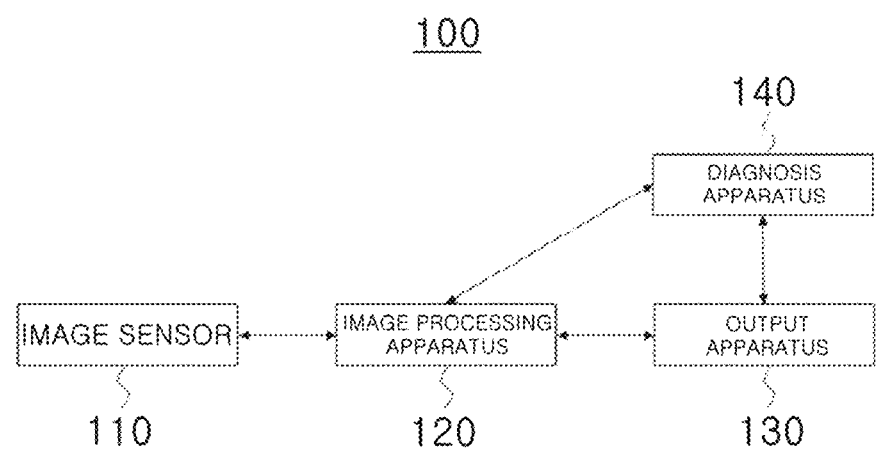
[FIG. 2]
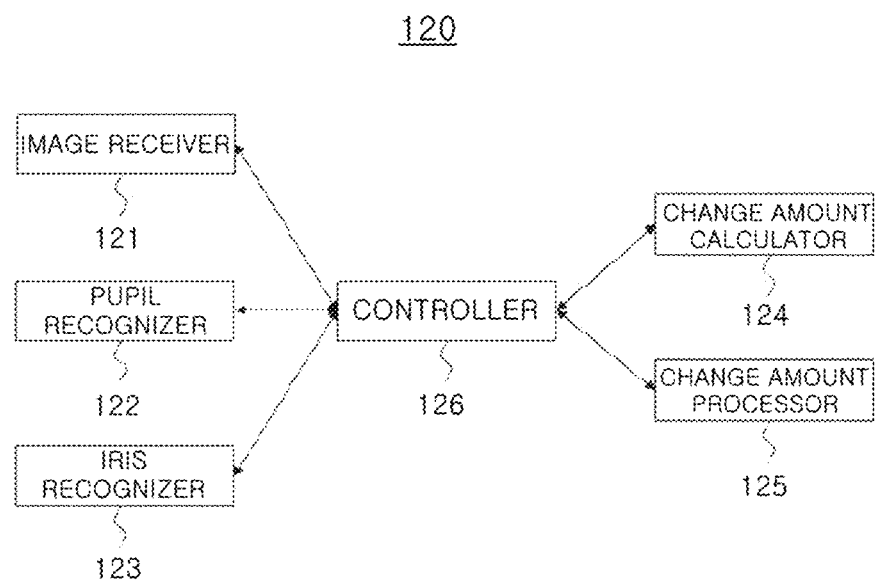

[FIG. 3]
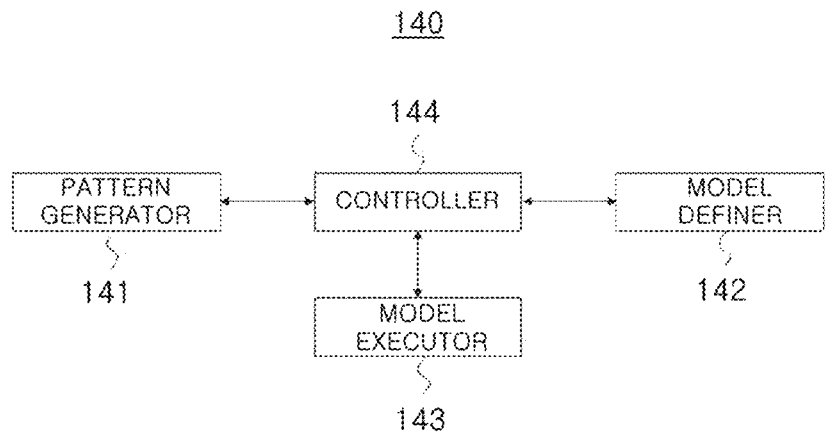
[FIG. 4]
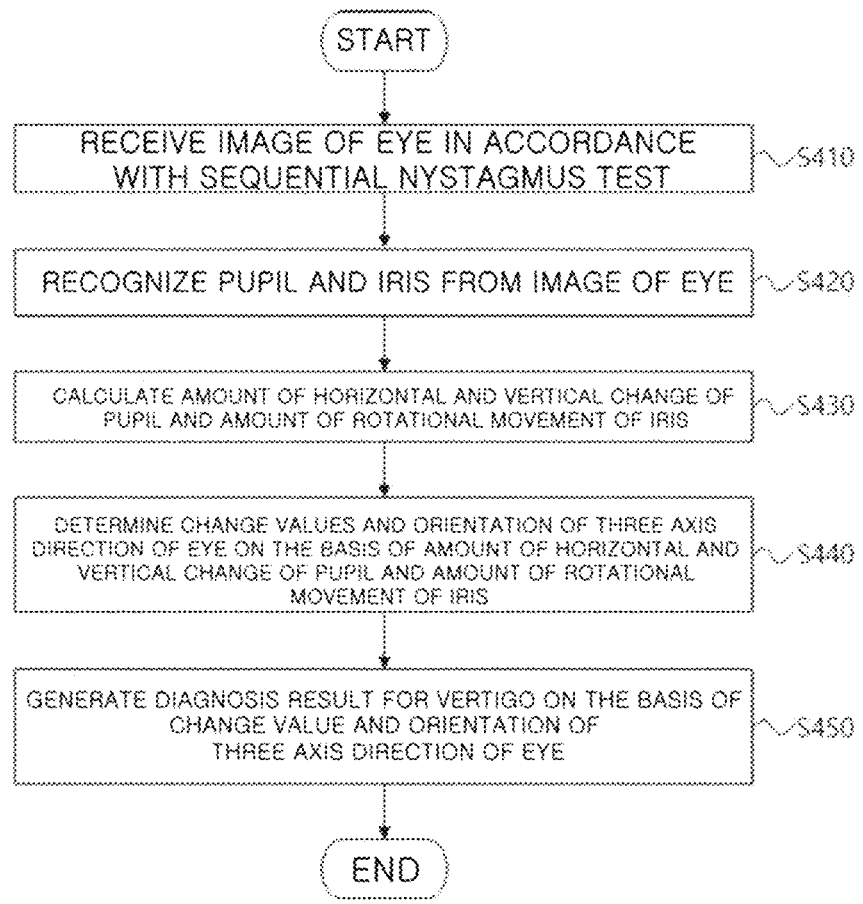

[FIG. 5]
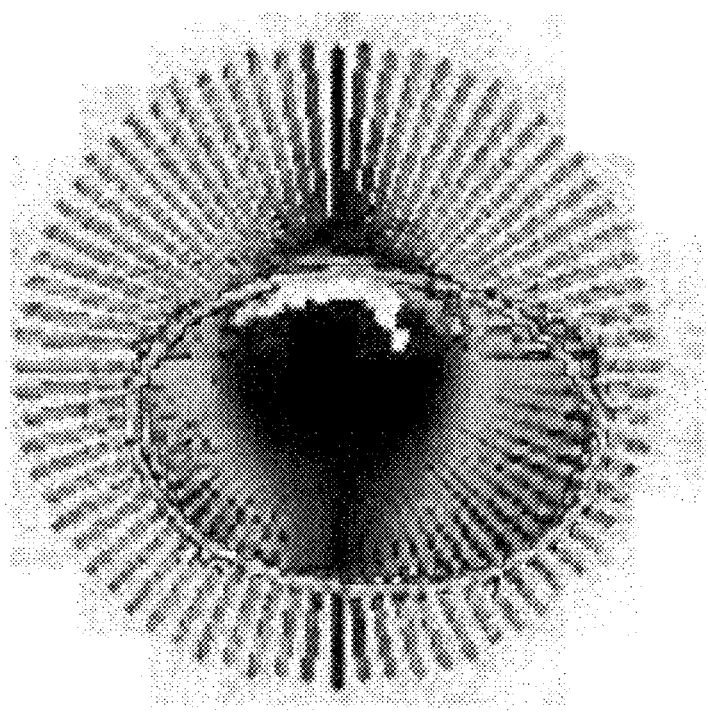
[FIG. 6]
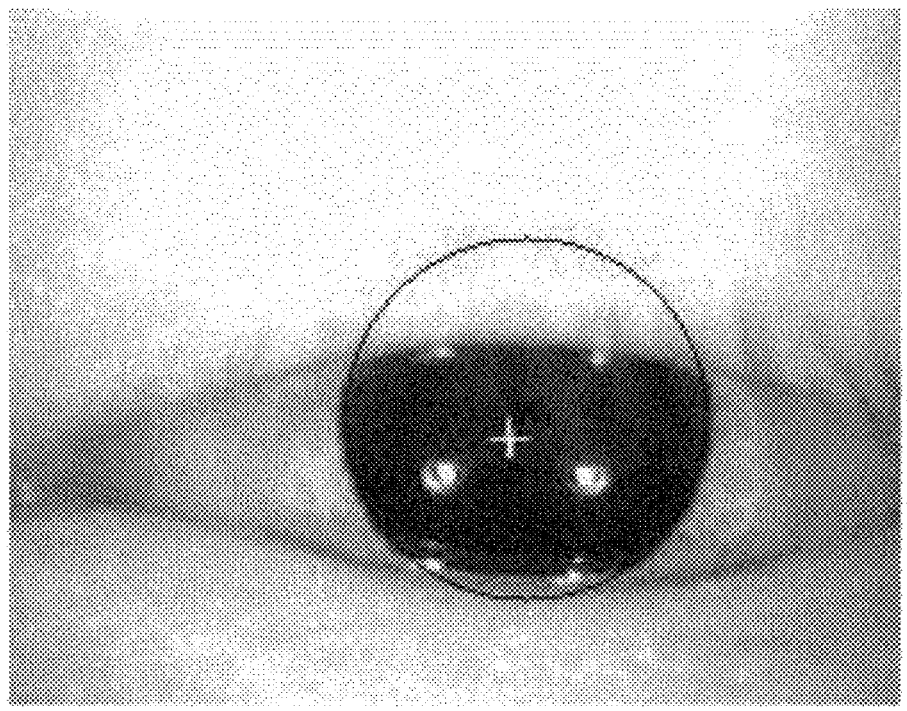

[FIG. 7]
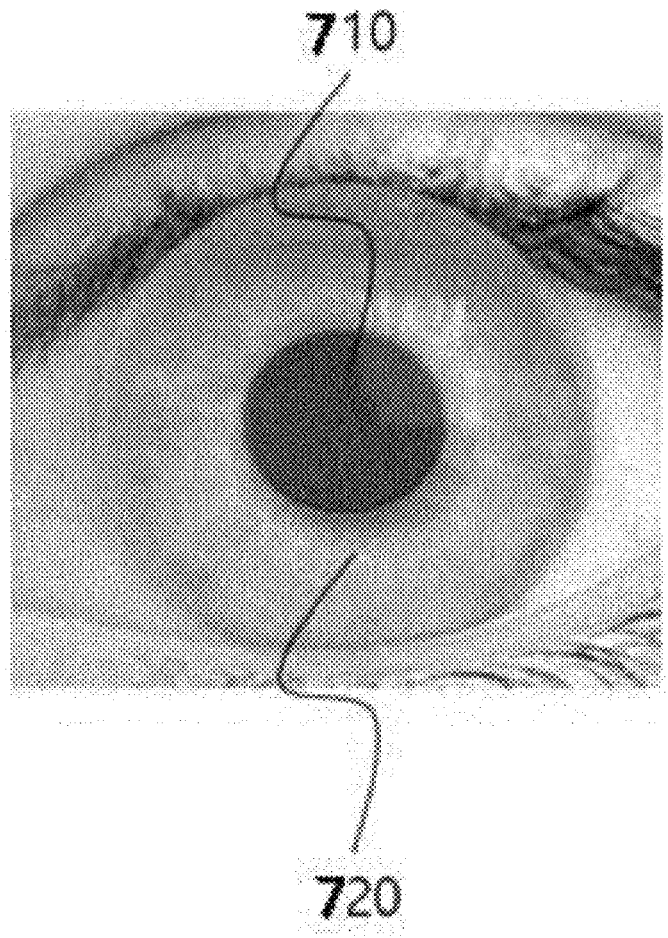
[FIG. 8]
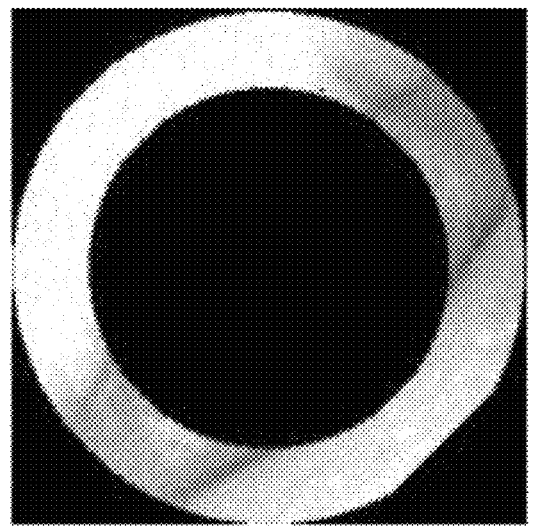

[FIG. 9]
[FIG. 10]
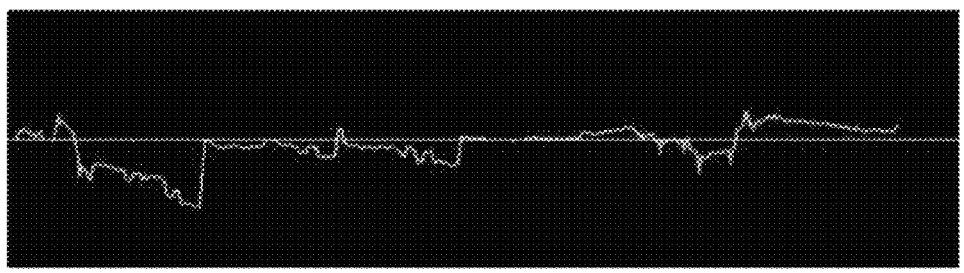

[FIG. 11]
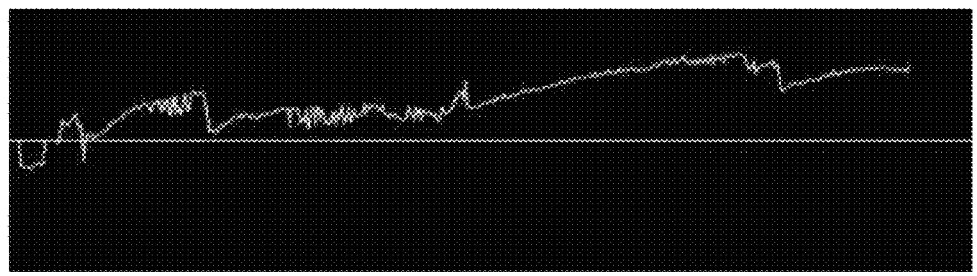
[FIG. 12]
[FIG. 13]
[FIG. 14]
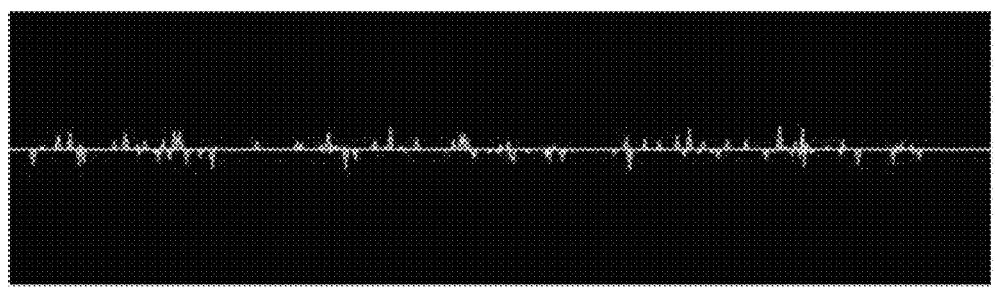

[FIG. 15]
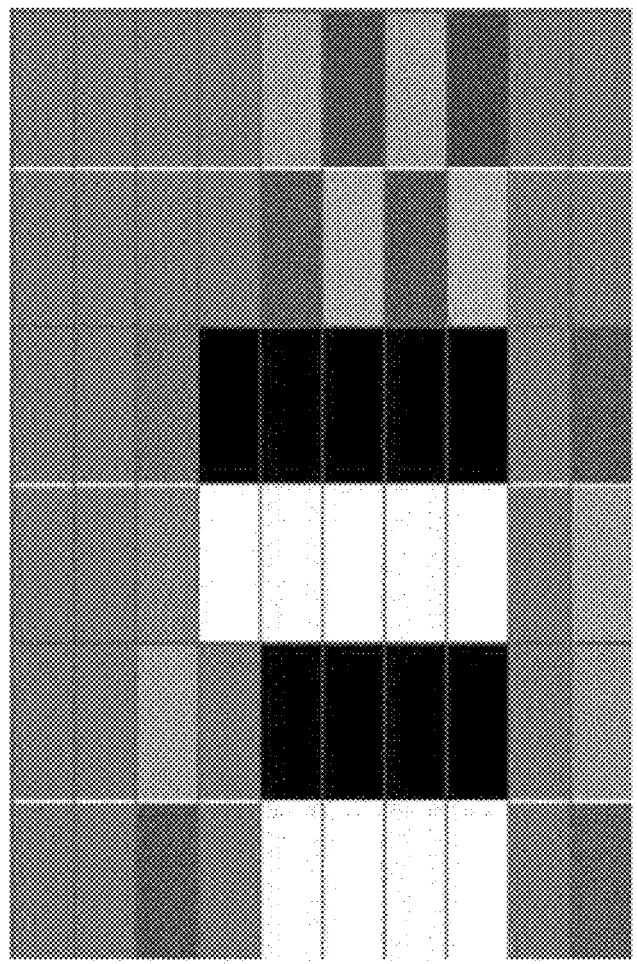

[FIG. 16]
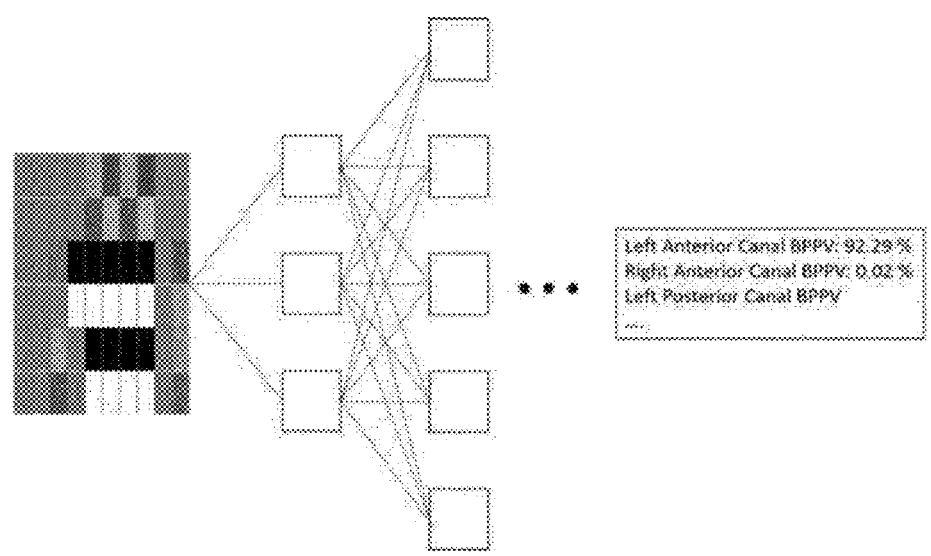

3-DIMENSIONAL MEASUREMENT METHOD FOR EYE MOVEMENT AND FULLY AUTOMATED DEEP-LEARNING BASED SYSTEM FOR VERTIGO DIAGNOSIS

TECHNICAL FIELD

The present invention relates to a technology for vertigo diagnosis, and more specifically, to an eye movement measurement and diagnostic methods and system which acquire the amounts of horizontal and vertical changes of eye movements and the orientation of torsional by processing an image captured through a video-Nystagmoscope (video goggle) used in vertigo diagnosis and provide diagnostic information on the basis of the acquired information.

BACKGROUND ART

Vertigo can be largely classified into one caused by central nervous system or one caused by peripheral nervous system, and it is known that specific type of vertigo has a unique type of eye movement pattern. The semicircular canal of a human body recognizes the rotational angular acceleration with respect to X, Y, and Z-axes in the three-dimensional space and the otolith organs serve as gyro sensors that recognize the horizontal and vertical linear accelerations and transmit relevant signals to the central nervous system. These vestibular signals, which are transmitted to the central nervous system in accordance with a change in head position, are associated with vision and lead to the vestibulo-ocular reflex that maintains balance when the body moves. If there are abnormalities in the semicircular canal, the otolith organs, or the vestibular nerves or associated central structures that control the semicircular canal and the otolith organs, proper vestibulo-ocular reflex does not occur and it becomes difficult for the body to maintain balance. Therefore, in patients who complain of dizziness, specific eye (abnormal) movements are caused by an aletration of the vestibulo-ocular reflex. Hence, in clinical practice, whether an abnormality in eye movements in accordance with a change in head position occurs is tested and the result is used for diagnosis.

The eye moves in three-dimensions, including movements about a horizontal axis and a vertical axis and a torsional movement associated with vestibular reflex. To date, the measurement of the amount of the movements of the eye has been generally performed through observation with eyes of an examiner or performed using Frenzel glasses, an electrical nystagmoscope, or a video-nystagmoscope. In the method of direct observation by the examiner or the use of the Frenzel glasses, eye movements may be observed when the amount of change in the nystagmus is large, but the measurement may be difficult in the opposite case. Nevertheless, the videonystagmoscope is widely in use as a diagnostic method even now. In this regard, there are a method in which a user makes a diagnosis by observing eye movements through a video and a method in which three-axis measurements of the horizontal, vertical, and torsional movements are displayed through a graph by using a nystagmus testing device attached to the videonystagmoscope and the measurement results are used for diagnosis. In the latter case, while it is possible to perform objective measurement, the amount of three-axis eye movements is measured by processing images obtained through an internally mounted separate image sensor in order to perform a 3-axis analysis. Accordingly, the sensitivity is determined depending on the resolution, frame rate, and image processing accuracy of the internally mounted image sensor, and the cost is high due to the technical complexity of separately measuring an angular velocity (deg/sec) with respect to each axis of the eye movements so that it is difficult to generally use the latter method. On the other hand, a simple videonystagmoscope without the above-described functions is relatively inexpensive and thus is widely used, but a diagnosis through this videonystagmoscope requires a high level of training.

Meanwhile, it may be difficult to diagnose central vertigo in patients with cerebellar infarction since their symptoms are similar to early symptoms of peripheral vertigo. In this case, diagnostic sensitivity of the observation of nystagmus has proven to be superior to that of early magnetic resonance imagining (MRI), and the observation of nystagmus and correct interpretation are important for the patients with vertigo.

PRIOR ART DOCUMENTS

Patent Documents (Patent Document 1) Korean Patent Registration No. 10-1297330

(Patent Document 2) Korean Laid-Open Patent Publication No. 10-2004-0107677

DISCLOSURE

Technical Problem

One objective of the present invention is to provide an eye movement measurement and diagnostic method and -system which measure eye movements in three axes by processing images acquired from an image sensor and determine and provide a probable diagnosis to a user on the basis of the eye movements.

Another objective of the present invention is to provide an eye movement measurement and diagnostic-method and -system which capture eye movements caused by various nystagmus tests conducted for diagnostic examination, measure a velocity and a direction for the amounts of horizontal/vertical changes in movement of a pupil of the eye from a reference position, measure a velocity and an orientation for the amount of a torsional movement of an iris of the eye, present quantitative measurement indicators for vertigo diagnosis, and automatically output a probable diagnosis by using a deep learning technology. Particularly, characteristic aspects of nystagmus in central vertigo are determined and the relevant information may be provided.

Technical Solution

According to a first aspect of the present invention to achieve the above objectives, there is provided an eye movement measurement and diagnostic method including the steps of: (a) sequentially presenting standardized test items for observation of nystagmus and receiving an image of an eye acquired for each of the test items; (b) recognizing a pupil and an iris from the image of the eye; (c) calculating amounts of horizontal and vertical changes of the pupil and an amount of torsional movement of the iris; (d) determining change values and orientations for three axis directions of the eye on the basis of the amounts of the horizontal and vertical changes of the pupil and the amount of the torsional movement of the iris; and (e) generating a diagnosis result for vertigo on the basis of the change values and orientations of the three axis directions of the eye.

The step (a) may include sequentially outputting information about an order and method of testing the standardized test items and instructing a user to conduct the test.

The step (b) may include identifying whether a circular-shaped object exists in the image of the eye, when the circular-shaped object exists, removing pixel values of a region except for the pupil using a pixel mean value of an interior of the circular-shaped object, collecting each pixel value while proceeding from a center of a region estimated as a pupil to a periphery thereof, wherein pixel values of the region except for the pupil have been removed from the region estimated as a pupil, and determining a pupil region using the collected pixel values.

The step (b) may include determining that a region of the circular-shaped object except for the pupil region is an iris region and converting the iris region into a horizontal or vertical image.

The step (c) may include calculating a horizontal change component and a vertical change component of a position of a center of the pupil by comparing the position of the center of the pupil with a pre-stored reference center position and calculating the amount of the rotational movement on the basis of a difference in coordinates between a position in the horizontal or vertical image of the iris and a matching position in a pre-stored reference image by comparing the horizontal or vertical image of the iris with the pre-stored reference image.

When the circular-shaped object is identified from the received image of the eye for the first time, the reference center position and the reference image may be set to be the center position of the pupil recognized from the image of the eye and the horizontal or vertical image of the iris recognized from the image of the eye.

The step (d) may include, on the basis of the amounts of the horizontal and vertical changes of the pupil and the amount of the rotational movement of the iris which are stored by repeating the steps (a) to (c), calculating representative values for the three axis directions after classifying values of change components in a predetermined direction into positive numbers and negative numbers and removing a value of a change component having a frequency lower than a predetermined frequency, and determining the change values and orientations for the three axis directions on the basis of the representative values for the three axis directions.

The eye movement measurement and diagnostic method may further include outputting the change values and orientations for the three axis directions of the eye, wherein the amounts of the horizontal and vertical changes of the pupil and the amount of the torsional movement of the iris, which are calculated by repeating the steps (a) to (c), are output.

The step (e) may include generating a pattern on the basis of the change values and orientations for the three axis directions of the eye which are obtained by repeating the steps (a) to (d), defining a deep learning model on the basis of the pattern, and determining a vertigo diagnosis using the defined deep learning model on the basis of change values and orientations for three axis directions of an eye of a predetermined patient.

According to a second aspect of the present invention to achieve the above objective, there is provided an eye movement measurement and diagnosis system including an image processing apparatus and a diagnosis apparatus, wherein the image processing apparatus comprises an image receiver configured to receive an image of an eye; a pupil recognizer configured to recognize a pupil from the image of the eye; an iris recognizer configured to recognize an iris from the image of the eye; a change amount calculator configured to calculate amounts of horizontal and vertical changes of the pupil and an amount of rotational movement of the iris; and a change amount processor configured to determine change values and orientations of three axis directions of the eye on the basis of the amounts of the horizontal and vertical changes of the pupil and the amount of the rotational movement of the iris, and wherein the diagnosis apparatus generates a diagnosis result for vertigo on the basis of the change values and orientations of the three axis directions of the eye received from the image processing apparatus.

The iris recognizer may identify whether a circular-shaped object exists in the image of the eye, and when the circular-shaped object exists, remove pixel values of a region except for the pupil using a pixel mean value of an interior of the circular-shaped object, collect each pixel value while proceeding from a center of a region estimated as a pupil to a periphery thereof, wherein pixel values of the region except for the pupil have been removed from the region estimated as a pupil, and determine a pupil region using the collected pixel values.

The iris recognizer may determine that a region of the circular-shaped object except for the pupil region is an iris region and convert the iris region into a horizontal or vertical image.

The change amount calculator may calculate a horizontal change component and a vertical change component of a center position of the pupil by comparing the center position of the pupil with a pre-stored reference center position and calculate the amount of the rotational movement on the basis of a difference in coordinates between a position in the horizontal or vertical image of the iris and a matching position in a pre-stored reference image by comparing the horizontal or vertical image of the iris with the pre-stored reference image.

When the circular-shaped object is identified from the received image of the eye for the first time, the reference center position and the reference image may be set to the center position of the pupil recognized from the image of the eye and the horizontal or vertical image of the iris recognized from the image of the eye.

The change amount processor may calculate, on the basis of the amounts of the horizontal and vertical changes of the pupil and the amount of the rotational movement of the iris which are stored by repeating the steps (a) to (c), representative values for the three axis directions after classifying values of change components in a predetermined direction into positive numbers and negative numbers, remove a value of a change component having a frequency lower than a predetermined frequency, and determine the change values and orientations for the three axis directions on the basis of the representative values for the three axis directions.

The eye movement measurement and diagnosis system may further include an output apparatus configured to output the change values and orientations for the three axis directions of the eye, wherein the output apparatus outputs the amounts of the horizontal and vertical changes of the pupil and the amount of the rotational movement of the iris which are calculated by repeating operations of the image receiver, the pupil recognizer, the iris recognizer, and the change amount calculator.

The diagnosis apparatus may include a pattern generator configured to generate a pattern on the basis of the change values and orientations for the three axis directions of the eye which are obtained by repeating operations of the image receiver, the pupil recognizer, the iris recognizer, the change amount calculator, and the change amount processor, a model definer configured to define a deep learning model on the basis of the pattern, and a model executor configured to determine a vertigo diagnosis using the defined deep learning model on the basis of change values and orientations for three axis directions of an eye of a predetermined patient.

Advantageous Effects

As described above, according to the present invention, torsional movement of an eye is analyzed so that eye movements in three axes that correspond to horizontal/vertical directions and torsional can be accurately determined through only processing in a software manner using an inexpensive video-nystagmoscope (video goggles).

In addition, signals that are difficult to visually identify are quantified and provided and a direction and a trend towards the direction are provided as objective indicators to indicate the direction of the eye movements among the up, down, left, and right directions so that symptoms can be easily and accurately determined.

Further, a probable diagnosis is presented by analyzing the eye movements so that a method and system according to the present invention may be effectively used in distinguishing between central vertigo and peripheral vertigo in an emergency room or the like where a neurotologist is not present.

DESCRIPTION OF DRAWINGS

FIG. 1 is a configuration diagram illustrating an eye movement measurement system according to an exemplary embodiment of the present invention.

FIG. 2 is a block diagram illustrating an image processing apparatus according to one embodiment.

FIG. 3 is a block diagram illustrating a diagnosis apparatus according to one embodiment.

FIG. 4 is a flowchart illustrating an eye movement measurement and diagnosis method according to one embodiment.

FIGS. 5 to 9 are example illustrations for describing a method of recognizing a pupil region and an iris region.

FIGS. 10 to 14 are example graphs for describing a method of calculating amounts of horizontal and vertical changes and an amount of rotational movement.

FIGS. 15 and 16 are example diagrams for describing a method of generating a diagnosis result for vertigo.

MODES OF THE INVENTION

Hereinafter, advantages and features of the present invention and methods of accomplishing the same may be understood more readily by reference to the following detailed description of exemplary embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the present invention will only be defined by the appended claims. Like reference numerals refer to like elements throughout the specification. As used herein the term "and/or" includes any and all combinations of one or more of the associated listed items.

Identification letters (e.g., a, b, c, etc.) in respective steps or operations are used for the sake of explanation and do not imply any particular order. Each operation may be performed in an order different from a specified order as long as a specific order is not explicitly and contextually specified. That is, each process may be performed in the same order as the specified order, performed substantially simultaneously, or performed in reverse order.

The terminology used herein is for the purpose of describing particular embodiments only and is not intended to be limiting to the invention. As used herein, the singular forms are intended to include the plural forms as well, unless the context clearly indicates otherwise. It will be further understood that the terms "comprises" and/or "comprising" used in this specification specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A detailed description of known functions and configurations incorporated herein will be omitted when it may obscure the subject matter with unnecessary detail. These terms are defined in consideration of functions according to the exemplary embodiments and can be varied according to a purpose of a user or manager, or precedent and so on. Therefore, definitions of the terms should be made on the basis of the overall context.

FIG. 1 is a configuration diagram illustrating an eye movement measurement and diagnosis system according to an exemplary embodiment of the present invention.

Referring to FIG. 1, an eye movement measurement and diagnosis system 100 includes an image sensor 110, an image processing apparatus 120, an output apparatus 130, and a diagnosis apparatus 140.

The image sensor 110 is an apparatus for imaging movements of an eye. Preferably, the image sensor 110 may acquire a reflected image through a light emitting diode (LED) when a patient is in a dark environment (e.g., when the patient is wearing goggles or in a darkroom) or may acquire a reflected image through visible rays when the patient is in a bright environment. The image sensor 110 used in the present invention is not limited in its type.

The image processing apparatus 120 is an apparatus for measuring eye movements by processing an image of an eye provided from the image sensor 110. Preferably, the image processing apparatus 120 may recognize a pupil and an iris from the image of the eye provided from the image sensor 110, analyze amounts of changes in movements of the pupil and iris, and ultimately provide the direction and velocity of the movement. In one embodiment, the image processing apparatus 120 may have a user interface to provide real-time measurement information of eye movement in individual frames of the image of the eye. For example, the image processing apparatus 120 may confirm, in real time, information about the instantaneous velocity and direction at a specific point in time with respect to a horizontal direction, a vertical direction, and rotation, a position of the pupil center, an image of an iris region, a pixel average of all pixels of an image of the iris region or the entire image, an ellipticity angle for an eye approximated to an ellipse rather than a circle, and the size of a rectangle enclosing the iris region.

The output apparatus 130 is an apparatus for outputting measurement information of eye movements provided through the image processing apparatus 120. Preferably, the output apparatus 130 may output a measurement value of the eye movement for each of the individual frames in real time or may output an analytic value ultimately obtained by analyzing the eye movement information and a symbol representing the analytic value. Here, the output apparatus 130 is described as being provided separately, but the output apparatus 130 may be included in the image processing apparatus 120 or the diagnosis apparatus 140, which will be described below, as a user interface thereof.

The diagnosis apparatus 140 is an apparatus for patterning quantified representative values of the eye movements provided from the image processing apparatus 120 and diagnosing vertigo based on a pattern. Preferably, the diagnosis apparatus 140 may receive representative values for a horizontal direction, a vertical direction, and rotation, which are obtained after all the frames in one image for the eye movement are processed, pattern representative values obtained from a plurality of images of the eye of a specific patient (e.g., eye images for each of various postures of the patient), and diagnose vertigo using a deep learning model on the basis of the pattern. Here, a result of vertigo diagnosis obtained through the diagnosis apparatus 140, i.e., a diagnosis with the highest probability or a probability of each individual diagnosis, may be output through the output apparatus 130.

FIG. 2 is a block diagram illustrating an image processing apparatus according to one embodiment.

Referring to FIG. 2, the image processing apparatus 120 includes an image receiver 121, a pupil recognizer 122, an iris recognizer 123, a change amount calculator 124, a change amount processor 125, and a controller 126. Preferably, the controller 126 controls operations and data flows of the image receiver 121, the pupil recognizer 122, the iris recognizer 123, the change amount calculator 124, and the change amount processor 125. Hereinafter, an operation performed by each component of the image processing apparatus 120 will be described in detail with reference to FIG. 4.

Referring to FIG. 4, the image receiver 121 receives an image of an eye (operation S410). First, test items are sequentially presented to a user so that the user can perform the standardized nystagmus test, and the user is instructed to perform the test. That is, a function for providing the sequential test order and a test method may be output to the user (practitioner), which may be performed by the image processing apparatus 120 or the diagnosis apparatus 140. For example, when a patient wearing a videonystagmoscope commences the test, the diagnosis apparatus 140 may sequentially inform of the tests to be performed, for example, in the order of "1) spontaneous nystagmus test, 2) gaze nystagmus test, 3) head-shaking nystagmus test, and 4) positioning and positional nystagmus test," and instruct the user to perform each test, and a test method for each test item may be output as a picture and text.

When a test is completed for each test item, nystagmus data obtained in accordance with each test item may be received, and preferably, the image receiver 121 may receive, from the image sensor 110, images of the eye that the image sensor 110 acquires as each test is performed. Here, the image receiver 121 may receive real-time images acquired from the image sensor 110 or receive pre-stored images acquired from the image sensor 110.

The pupil recognizer 122 recognizes a pupil from the eye image, and the iris recognizer 123 recognizes an iris from the eye image (operation S420). Preferably, the pupil recognizer 122 may first determine whether a circular-shaped object exists in the eye image. In this case, an image processing scheme, such as circle Hough Transform (CHT), may be applied to determine whether the circular shaped object exists in the image. More specifically, the pupil recognizer 122 may identify whether there is a circular-shaped region in the eye image, and an open state may be set when there is a circular-shaped region in the image and a closed state may be set when there is no region similar to a circle in the image. Here, setting information of the open state or closed state may be displayed on the output apparatus 130 connected to the image processing apparatus 120.

Preferably, when it is identified that there is a circular-shaped object (i.e., when the open state is set), the pupil recognizer 122 may remove pixel values for a region except for a pupil using a pixel mean value of an interior of the circular-shaped object. More specifically, the pupil recognizer 122 converts the circular-shaped object into grayscale such that all pixel values are within a range of 0 to 255, determines that an object recognized as a circle is a pupil, and extracts a rectangular area enclosing the recognized circle. Since most of the rectangular area corresponds to the pupil, the pupil recognizer 122 may calculate a mean of all pixel values of the rectangular area, wherein the mean value, which is a statistical expectation value, becomes a threshold specifying the pupil. Then, the pupil recognizer 122 converts pixels having values larger than the threshold among the pixels in the rectangular area into white so that only pixels corresponding to the pupil remain black in the rectangular area. That is, binarization of pixels in the rectangular area is performed on the basis of the threshold so that the pixel values of the region except for the pupil are removed.

Preferably, the pupil recognizer 122 may collect each pixel value while proceeding from a center of a region estimated as a pupil to a periphery thereof, wherein pixel values of the region except for the pupil have been removed from the region estimated as a pupil, and determine a pupil region using the collected pixel values. More specifically, referring to FIG. 5, the pupil recognizer 122 collects values at pixel positions while proceeding from a center of a region estimated as a pupil to a periphery thereof by applying a cosine function to predetermined angles in a horizontal direction and applying a sine function to the predetermined angles in a vertical direction wherein the predetermined angles are obtained by dividing 0 to 360 degrees into predetermined units. For example, when the predetermined angle is 90 degrees and it is assumed that center coordinates of the pupil are (0, 0), a position at relative coordinates (1, 0) from the center coordinates is a position of the next coordinates since the sine 90 degrees is 1 and the cosine 90 degrees is 0, and when a difference between two pixel values at coordinates (0, 0) and (1, 0) exceeds a predetermined difference value, the collection may be stopped and a position of pixel coordinates for the predetermined angle may be stored. When the obtained positions of the pixel coordinates for the predetermined angle are approximated to an ellipse, a corresponding region may be determined to be a pupil region as shown in FIG. 6. In FIG. 6, a blue circle corresponds to a pupil region and a red circle corresponds to a center point of the pupil. In this case, in the case of approximation to an ellipse, an ellipticity angle may be calculated on the basis of a horizontal line or a vertical line.

After the pupil region is determined, the iris recognizer 123 may determine a region of the circular-shaped object except for the pupil region to be an iris region. Here, referring to FIG. 7, the iris region 720 is a flat torus shape excluding the pupil region 710. Then, the iris processing apparatus 120 may convert the iris region into a horizontal or vertical image. More specifically, the iris recognizer 123 may enlarge the pupil region obtained by the pupil recognizer 122 to a predetermined size as illustrated by a black circle in FIG. 8 and determine the iris region by removing the pupil region obtained by the pupil recognizer 122 from the enlarged region. Then, the iris recognizer 123 may convert the iris region into a horizontal or vertical image through coordinate conversion. For example, a vertical image of the iris region is as shown in FIG. 9.

In one embodiment, when the circular-shaped object is recognized in the eye image, the center position of the pupil region recognized in operation S420 and the horizontal or vertical image of the iris region may be set to a reference center position and a reference image, respectively, and may be used as reference values for calculating a change amount value in operation S430. More specifically, initialization to a close state takes place with respect to an image of an eye before the image receiver 121 receives the image of an eye from the image sensor 110. As the image receiver 121 receives the eye image, the image receiver 121 identifies whether there is a circular-shaped object in the eye image, and when it is identified that there is a circular-shaped object, an open state is set. The center position of the pupil recognized from the corresponding eye image at the time of shifting from the closed state to the open state is set to a reference center position, and the horizontal or vertical image of the iris recognized from the corresponding eye image is stored as a reference image. When the image receiver 121 receives the next eye image after the reference center position and the reference image are stored, a pupil and an iris are recognized again from the received eye image and movements of the pupil and the iris may be calculated in operation S430, which will be described below.

The change amount calculator 124 calculates amounts of horizontal and vertical changes of the pupil and an amount of rotational movement of the iris (operation S430). Preferably, the change amount calculator 124 may calculate a horizontal change component that corresponds to the left/right movement amount of the center position of the pupil and a vertical change component that corresponds to the up/down movements of the pupil by comparing a center position of the pupil with the pre-stored reference center position. For example, the horizontal change component is as shown in FIG. 10 and the vertical change component is as shown in FIG. 11. In FIG. 10, an x-axis represents time and a y-axis represents an absolute horizontal change value of the center of the pupil, and in FIG. 11, an x-axis represents time and a y-axis represents an absolute vertical change value of the center of the pupil. The horizontal change component and the vertical change component calculated as described above may be stored in the change amount calculator 124. The stored horizontal change component and vertical change component are differentiated to calculate the directions and velocities of the horizontal/vertical movements of the eye and the differential values are delivered to the change amount processor 125. For example, the differential value of the horizontal change component shown in FIG. 10 is the same as shown in FIG. 12 and the differential value of the vertical change component shown in FIG. 11 is the same as shown in FIG. 13. In this case, the differential value of the horizontal change component and the differential value of the vertical change component correspond to the amount of the horizontal change and the amount of the vertical change of the pupil, respectively.

In addition, the change amount calculator 124 may compare a horizontal or vertical image of the iris with the pre-stored reference image and calculate an amount of rotational movement based on a difference between a position in the horizontal or vertical image of the iris and a matching position in the reference image. For example, an image of the iris region is divided by a predetermined width in a vertical direction so that a plurality of vertical images of the iris having the same width but different vertical coordinate values are obtained. As described above, when image searching is performed on the reference image on the basis of the vertical images of the iris and matching coordinates are found in the reference image, a difference between a vertical coordinate value of the found coordinates and a vertical coordinate value of the coordinates of the vertical image of the iris may be calculated, as shown in FIG. 14. In FIG. 14, an x-axis represents time and a y-axis represents a rotation change amount obtained through the iris movements. The difference value obtained as described above is not differentiated, unlike the horizontal and vertical change components, and is directly delivered to the change amount processor 125. In this case, the difference value for the coordinates of the reference image and the horizontal or vertical image of the iris corresponds to the amount of the rotational movement.

The change amount processor 125 determines change values and orientations for three axis directions of the eye on the basis of the amounts of the horizontal and vertical changes of the pupil and the amount of the rotational movement of the iris (operation S440). Preferably, operations S410 to S430 are repeatedly performed and the change amount processor 125 may classify values of a change component in a specific direction into negative numbers and positive numbers on the basis of the plurality of amounts of horizontal and vertical changes of the pupil and the plurality of amounts of rotational movement of the iris which are stored by repeating operations S410 to S430, remove a value of the change component having the frequency lower than the predetermined frequency, and then calculate representative values for the three axis directions. In this case, the representative values for the three axis directions may be calculated for various posture-specific images of the patient by repeating operations S410 to S440.

More specifically, when the reception of images through the image receiver 121 is terminated, i.e., when no more images are received, the change amount processor 125 may determine that a moving image is terminated, set intermediate straight lines shown in FIGS. 12 to 14 to zero for the differential values (FIGS. 12 and 13) of the horizontal and vertical change components received from the change amount calculator 124 and the difference value (FIG. 14), classify the values of the change components in a specific direction among the left, right, up, and down directions into negative numbers and positive numbers, remove a value with the low frequency, and determine that the large absolute value obtained by adding or integrating all the positive values or all the negative values in each direction is a representative value of each of the three axis directions. For example, when, among the differential values of all the horizontal change components, the sum of the values that are positive numbers is 48 and the sum of the values that are negative numbers is −30, the representative value is 48 and the direction is the right direction.

The change amount processor 125 may determine the change values and orientations for the three axis directions on the basis of the acquired representative values for the three axis directions. For example, when the representative values for the three axis directions are obtained as −13 in a horizontal direction, 30 in a vertical direction, and −3 in a rotation direction, the change value may be determined to be −13 in the left direction and 30 in an upward direction and the orientation may be determined to be −3 in a counter-clockwise direction.

In one embodiment, the change values and orientations for the three axis directions of the eye acquired through operation S440 may be output through an outputter (not shown) of the image processing apparatus 120 or the output apparatus 130. In addition, the amounts of horizontal and vertical changes of the pupil and the amount of rotational movement of the iris which are calculated by repeating operations S410 to S430 may be output through the outputter or the output apparatus 130 each time the amounts are calculated or at predetermined intervals.

Then, a diagnosis result for vertigo is generated based on the change values and orientations for the three axis directions of the eye acquired through operation S440 (operation S450). Operation S450 is performed by the diagnosis apparatus 140 which receives information about the change values and orientations for the three axis directions of the eye acquired from the image processing apparatus 120, which will be described below with reference to FIG. 3.

FIG. 3 is a block diagram illustrating a diagnosis apparatus 140 according to one embodiment. Referring to FIG. 3, the diagnosis apparatus 140 includes a pattern generator 141, a model definer 142, a model executor 143, and a controller 144. Here, the controller 144 controls operations and a data flow of the pattern generator 141, the model definer 142, and the model executor 143.

Preferably, when the change values and orientation for the three axis directions of the eye, i.e., representative values of the horizontal direction, vertical direction, and rotation, in a plurality of moving images are received from the image processing apparatus 120, the pattern generator 141 of the diagnosis apparatus 140 may generate and store one representative pattern by integrating and combining the acquired representative values for the three axes in various posture-specific moving images of the patient. Here, what the representative values for the three axes, which constitute the pattern, represent may not necessarily correspond to the horizontal direction, the vertical direction, and the rotation and may change variously according to circumstances. For example, when three-axis representative values for a total of 10 posture-specific moving images are received, as shown in FIG. 15, a pattern may be formed by grids representing the three-axis representative values with brightness, a total of 10 postures are disposed in a width direction and two representative values for each of the three axes, i.e., a total of 6 grids, are disposed in a height direction so that one pattern consisting of a total of 30 grids can be generated. In FIG. 15, it is illustrated that the 3-axis representative values are represented as brightness, but various representations, such as the size of a grid or a color of a grid, may be possible. In this case, representative patterns may be separately stored in training, validation, and test sets and may be called in an arbitrary order.

Preferably, the model definer 142 may define a deep learning model for performing deep learning training on the representative patterns generated by the pattern generator 141. A variety of models for mapping the patterns and diagnoses may be used as the deep learning model, for example, convolutional neural network may be used. In addition, the diagnosis may be converted into categorical data or quantified data, and the model definer 142 may define a training optimization algorithm, a model structure, a method of storing and calling training data, and various hyper-parameters for the deep learning model that is represented by a combination of neurons and weights and perform deep learning training on the basis of the defined contents.

An individual processing unit of the deep learning model is a neuron and the deep learning model has a neural network structure in which neurons are connected. An individual neuron includes a numerical value corresponding to a weight and a portion where one neuron is connected to the next neuron is represented as an activation function. The activation function is a non-linear function and may include, for example, sigmoid, tan h, ReLU, and the like, and these functions determine which form a value is converted into when the value is delivered from one neuron to the next neuron. The neural network structure may be represented as a grid matrix w. For example, when training data obtained from the pattern generator 141 is X and a vertigo diagnosis is Y, a function that maps X and Y, i.e., a target function, has a form of Y=wX. Here, the target function yields a specific predicted value Y for an input pattern X. When a diagnosis made by a specialist for a specific patient is assumed to be true and represented as y, there may be a difference between a true value y and a deep learning model predicted value Y, and such a difference is referred to as a loss, which is an error between the reality and the model. The deep learning training is a process of reducing the loss value using backpropagation. One piece of training data may be composed of one representative pattern and a vertigo diagnosis made by a specialist and the deep learning training may be performed by breaking up the data into small training units, which correspond to batches, rather than being performed on all of the data at once. The repetitive backpropagation may be performed on individual batches and whether an error of the model that matches with the training set and the diagnosis is reduced and whether the diagnosis accuracy of the model is increased may be confirmed through the training loss value and validation accuracy, respectively. In this case, when the loss value is reduced or the accuracy is increased as compared to a previous model, the entire model or a weight matrix value representing the model may be stored in an arbitrary place.

Preferably, the model executor 143 may make a diagnosis for a pattern obtained through a moving image of a new patient by using the deep learning model defined by the model definer 142. The model executor 143 may execute a model with the lowest loss and the highest validation accuracy among the models generated by the model definer 142, determine a diagnosis (left anterior canal benign paroxysmal positional vertigo (BPPV)) of the highest probability by calculating an individual probability of each of various vertigo diagnoses using cross entropy calculation, as shown in FIG. 16, and determine a probability of the patient having specific vertigo symptoms. In this case, the determined diagnosis may be output as a diagnosis result to the output apparatus 130.

Meanwhile, the eye movement measurement and diagnosis method according to the embodiment of the present invention may be implemented as computer-readable code in a computer-readable recording medium. The computer-readable recording medium includes any type of recording device in which data that can be read by a computer system is stored.

For example, the computer-readable recording medium includes a read-only memory (ROM), a random-access memory (RAM), a compact disc read-only memory (CD-ROM), a magnetic tape, a hard disk, a floppy disk, a mobile storage device, a non-volatile memory (flash memory), an optical data storage device, etc.

Further, the computer readable recording medium can also be distributed over network coupled computer systems so that the computer readable code is stored and executed in a distributed fashion.

While the eye movement measurement and diagnosis method according to the present invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

| Reference Numerals | |
|---|---|
| 100: | EYE MOVEMENT MEASUREMENT SYSTEM |
| 110: | IMAGE SENSOR |
| 120: | IMAGE PROCESSING APPARATUS |
| 121: | IMAGE RECEIVER |
| 122: | PUPIL RECOGNIZER |
| 123: | IRIS RECOGNIZER |
| 124: | CHANGE AMOUNT CALCULATOR |
| 125: | CHANGE AMOUNT PROCESSOR |
| 126: | CONTROLLER |
| 130: | OUTPUT APPARATUS |
| 140: | DIAGNOSIS APPARATUS |
| 141: | PATTERN GENERATOR |
| 142: | MODEL DEFINER |
| 143: | MODEL EXECUTOR |
| 144: | CONTROLLER |

The invention claimed is:

1. An eye movement measurement and diagnostic method comprising the steps of:
   (a) presenting test items and receiving an image of an eye, which is acquired for each of the test items, for each test;
   (b) recognizing a pupil and an iris from the image of the eye;
   (c) calculating amounts of horizontal and vertical changes of the pupil and an amount of torsional movement of the iris;
   (d) determining change values and orientations for three axis directions of the eye on the basis of the amounts of the horizontal and vertical changes of the pupil and the amount of the torsional movement of the iris; and
   (e) generating a diagnosis result for vertigo on the basis of the change values and orientations of the three axis directions of the eye,
   wherein the step (b) comprises:
   identifying whether a circular-shaped object exists in the image of the eye; when the circular-shaped object exists, removing pixel values of a region except for the pupil using a pixel mean value of an interior of the circular-shaped object; and
   collecting each pixel value while proceeding from a center of a region estimated as a pupil to a periphery thereof, wherein pixel values of the region except for the pupil have been removed from the region estimated as a pupil, and determining a pupil region using the collected pixel values.

2. The eye movement measurement and diagnosis method of claim 1, wherein the step (b) comprises: determining that a region of the circular-shaped object except for the pupil region is an iris region; and converting the iris region into a horizontal or vertical image.

3. The eye movement measurement and diagnosis method of claim 1, wherein the step (c) comprises:
   calculating a horizontal change component and a vertical change component of a position of a center of the pupil by comparing the position of the center of the pupil with a pre-stored reference center position; and
   calculating the amount of the rotational movement on the basis of a difference in coordinates between a position in a horizontal or vertical image of the iris and a matching position in a pre-stored reference image by comparing the horizontal or vertical image of the iris with the pre-stored reference image.

4. The eye movement measurement and diagnosis method of claim 3, wherein, when a circular-shaped object is identified from the received image of the eye for the first time, the reference center position and the reference image are set to the center position of the pupil recognized from the image of the eye and the horizontal or vertical image of the iris recognized from the image of the eye.

5. An eye movement measurement and diagnostic method comprising the steps of:
   (a) presenting test items and receiving an image of an eye, which is acquired for each of the test items, for each test;
   (b) recognizing a pupil and an iris from the image of the eye;
   (c) calculating amounts of horizontal and vertical changes of the pupil and an amount of torsional movement of the iris;
   (d) determining change values and orientations for three axis directions of the eye on the basis of the amounts of the horizontal and vertical changes of the pupil and the amount of the torsional movement of the iris; and
   (e) generating a diagnosis result for vertigo on the basis of the change values and orientations of the three axis directions of the eye,
   wherein the step (d) comprises:
   on the basis of the amounts of the horizontal and vertical changes of the pupil and the amount of the torsional movement of the ins which are stored by repeating the steps (a) to (c), calculating representative values for the three axis directions after classifying values of change components in a predetermined direction into positive numbers and negative numbers and removing a value of a change component having a frequency lower than a predetermined frequency; and
   determining the change values and orientations for the three axis directions on the basis of the representative values for the three axis directions.

6. The eye movement measurement and diagnosis method of claim 1, further
   comprising outputting the change values and orientations for the three axis directions of the eye,
   wherein the amounts of the horizontal and vertical changes of the pupil and the amount of the torsional movement of the iris, which are calculated by repeating the steps (a) to (c), are output.

7. The eye movement measurement and diagnosis method of claim 1, wherein the step (e) comprises:
   generating a pattern on the basis of the change values and orientations for the three axis directions of the eye which are obtained by repeating the steps (a) to (d);

defining a deep learning model on the basis of the pattern; and determining a vertigo diagnosis using the defined deep learning model on the basis of change values and orientations for three axis directions of an eye of a predetermined patient.

8. An eye movement measurement and diagnosis system comprising: an image processing apparatus; and
a diagnosis apparatus,
wherein the image processing apparatus comprises:
an image receiver configured to receive an image of an eye acquired for each test item;
a pupil recognizer configured to recognize a pupil from the image of the eye; an iris recognizer configured to recognize an iris from the image of the eye; a change amount calculator configured to calculate amounts of horizontal and
vertical changes of the pupil and an amount of rotational movement of the iris; and
a change amount processor configured to determine change values and orientations of three axis directions of the eye on the basis of the amounts of the horizontal and vertical changes of the pupil and the amount of the torsional movement of the iris, and
wherein the diagnosis apparatus generates a diagnosis result for vertigo on the basis of the change values and orientations of the three axis directions of the eye received from the image processing apparatus,
wherein the iris recognizer is configured to:
identify whether a circular-shaped object exists in the image of eye;
when the circular-shaped object exists remove pixel values of a region except for the pupil using a pixel mean value of an interior of the circular-shaped object;
collect each pixel value while proceeding from a center of a region estimated as a pupil to a periphery thereof, wherein pixel values of the region except for the pupil have been removed from the region estimated as a pupil, and
determine a pupil region using the collected pixel values.

9. The eye movement measurement and diagnosis system of claim 8, wherein the iris recognizer is configured to determine that a region of the circular-shaped object except for the pupil region is an iris region and convert the iris region into a horizontal or vertical image.

10. The eye movement measurement and diagnosis system of claim 8, wherein the change amount calculator is configured to:
calculate a horizontal change component and a vertical change component of a center position of the pupil by comparing the center position of the pupil with a pre-stored reference center position; and
calculate the amount of the torsional movement on the basis of a difference in coordinates between a position in a horizontal or vertical image of the ins and a matching position in a pre-stored reference image by comparing the horizontal or vertical image of the ins with the pre-stored reference image.

11. The eye movement measurement and diagnosis system of claim 10, wherein, when a circular-shaped object is identified from the received image of the eye for the first time, the reference center position and the reference image are set to the center position of the pupil recognized from the image of the eye and the horizontal or vertical image of the iris recognized from the image of the eye.

12. The eye movement measurement and diagnosis system of claim 8, wherein the change amount processor is configured to:
calculate, on the basis of the amounts of the horizontal and vertical changes of the pupil and the amount of the rotational movement of the iris which are stored by repeating the steps (a) to (c), representative values for the three axis directions after classifying values of change components in a predetermined direction into positive numbers and negative numbers;
remove a value of a change component having a frequency lower than a predetermined frequency; and
determine the change values and orientations for the three axis directions on the basis of the representative values for the three axis directions.

13. The eye movement measurement and diagnosis system of claim 8, further comprising an output apparatus configured to output the change values and orientations for the three axis directions of the eye,
wherein the output apparatus outputs the amounts of the horizontal and vertical changes of the pupil and the amount of the rotational movement of the iris which are calculated by repeating operations of the image receiver, the pupil recognizer, the iris recognizer, and the change amount calculator.

14. The eye movement measurement and diagnosis system of claim 8, wherein the diagnosis apparatus comprises:
a pattern generator configured to generate a pattern on the basis of the change values and orientations for the three axis directions of the eye which are obtained by repeating operations of the image receiver, the pupil recognizer, the iris recognizer, the change amount calculator, and the change amount processor;
a model definer configured to define a deep learning model on the basis of the pattern; and
a model executor configured to determine a vertigo diagnosis using the defined deep learning model on the basis of change values and orientations for three axis directions of an eye of a predetermined patient.

15. A computer-readable recording medium having a program recorded thereon, wherein the method according to claim 1 is performable in a computer by using the program.

* * * * *